United States Patent
Meyer et al.

(10) Patent No.: US 11,223,939 B1
(45) Date of Patent: Jan. 11, 2022

(54) ENVIRONMENTAL CONDITIONS MONITORING SYSTEM

(71) Applicant: UIPCO, LLC, San Antonio, TX (US)

(72) Inventors: Gregory Brian Meyer, San Antonio, TX (US); Mark Anthony Lopez, Helotes, TX (US); Ravi Durairaj, San Antonio, TX (US); Nolan Serrao, Plano, TX (US); Victor Kwak, Frisco, TX (US); Ryan Thomas Russell, The Colony, TX (US); Christopher Russell, The Colony, TX (US); Ruthie D. Lyle, Durham, NC (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 16/943,616

(22) Filed: Jul. 30, 2020

Related U.S. Application Data

(60) Provisional application No. 62/881,079, filed on Jul. 31, 2019.

(51) Int. Cl.
| | |
|---|---|
| *H04W 4/90* | (2018.01) |
| *H04W 4/029* | (2018.01) |
| *H04W 4/02* | (2018.01) |
| *G16H 40/63* | (2018.01) |

(52) U.S. Cl.
CPC .............. *H04W 4/90* (2018.02); *G16H 40/63* (2018.01); *H04W 4/025* (2013.01); *H04W 4/029* (2018.02)

(58) Field of Classification Search
CPC ................................. G08B 21/088; H04B 1/38
See application file for complete search history.

(56) References Cited

U.S. PATENT DOCUMENTS

| | | | |
|---|---|---|---|
| 10,159,849 B2* | 12/2018 | Kaib .................... | G08B 25/016 |
| 10,741,048 B1* | 8/2020 | Foster .................. | A61B 5/7455 |
| 2003/0030544 A1* | 2/2003 | Smith ................... | G09B 21/00 |
| | | | 340/407.1 |
| 2004/0046667 A1* | 3/2004 | Copley .............. | G08B 21/0286 |
| | | | 340/573.4 |
| 2015/0164351 A1* | 6/2015 | He .......................... | A61B 5/11 |
| | | | 702/19 |
| 2018/0075716 A1* | 3/2018 | Mirov ..................... | G08B 6/00 |
| 2018/0206100 A1* | 7/2018 | Eisner ................. | G06F 16/284 |

* cited by examiner

*Primary Examiner* — Qutbuddin Ghulamali
(74) *Attorney, Agent, or Firm* — Plumsea Law Group, LLC

(57) ABSTRACT

A conditions monitoring system may include a system controller. The controller may include a device processor and a non-transitory computer readable medium. The computer readable medium may include instructions executable by the device processor to perform the following steps: receiving positional data from a wearable device of a wearer; receiving physical data regarding the wearer from the wearable device; making a determination of a possible dangerous condition based on the data received from the wearable device; and providing instructions to the wearable device for the wearer to follow to avoid danger related to the dangerous condition.

19 Claims, 5 Drawing Sheets

ENVIRONMENTAL CONDITIONS MONITORING SYSTEM

CROSS-REFERENCE TO RELATED APPLICATIONS

This application claims priority to Meyer et al., U.S. Provisional Application No. 62/881,079, filed Jul. 31, 2019, and entitled "Environmental Conditions Monitoring System," the entire disclosure of which is incorporated herein by reference.

TECHNICAL FIELD

The present disclosure generally relates to a system for detecting dangerous conditions and, more particularly, to a system that utilizes data collected by wearable devices to detect dangerous conditions.

BACKGROUND

Dangerous conditions, for example from weather, natural disasters, and other public emergencies can be dangerous to individuals particularly without advanced notice. In some cases, dangerous conditions may approach individuals and reach a very close proximity to the individuals before the individual becomes aware of the danger. For example, some thunderstorms develop very quickly and/or may travel rapidly across the countryside. Further, even with sufficient notice of the dangerous conditions, individuals may not know how to avoid the danger, particularly when the conditions are moving in their direction.

Further, certain conditions may cause other conditions that may be dangerous. For example, heavy rain storms may cause flooding, which can pose a secondary danger. Flooding occurs in a particular geographic area and affects individuals with precision. I.e., either the individual is in the flood area (e.g., flood plain) or they are not. Thus, flooding may be predicted based on factors such as rainfall. Individuals may benefit from early notice and guidance as to how to avoid the flooding.

There is a need in the art for systems and methods that address the shortcomings discussed above. In particular, there is a need in the art for conditions monitoring systems.

SUMMARY

In one aspect, the present disclosure is directed to a conditions monitoring system including a system controller. The controller may include a device processor and a non-transitory computer readable medium. The computer readable medium may include instructions executable by the device processor to perform the following steps: receiving positional data from a wearable device of a wearer; receiving physical data regarding the wearer from the wearable device; making a determination of a possible dangerous condition based on the data received from the wearable device; and providing instructions to the wearable device for the wearer to follow to avoid danger related to the dangerous condition.

In another aspect, the present disclosure is directed to a conditions monitoring system including a system controller. The system controller may include a device processor; and a non-transitory computer readable medium including instructions executable by the device processor to perform the following steps: receiving positional data from a wearable device of a wearer; receiving atmospheric data regarding the atmospheric in proximity to the wearer; making a determination of a possible dangerous condition based on the data received from the wearable device; and providing instructions to the wearable device for the wearer to follow to avoid danger related to the dangerous condition.

In another aspect, the present disclosure is directed to a conditions monitoring system including a system controller. The system controller may include a device processor; and a non-transitory computer readable medium including instructions executable by the device processor to perform the following steps: receiving positional data from a wearable device of a wearer; receiving atmospheric data regarding the atmospheric in proximity to the wearer; making a determination of a primary condition based on the data received from the wearable device; inferring, from the primary condition, a secondary condition related to the primary condition; and providing instructions to the wearable device for the wearer to follow to avoid danger related to the secondary condition.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

The disclosed condition monitoring systems may include several features for assisting persons who are subject to danger related to the monitored conditions. For example, the disclosed systems may be configured to monitor data from wearable devices, such as smart watches and fitness bands, to determine the presence of various environmental conditions, including dangerous conditions. It will be understood that, for purposes of this specification and claims, the term "environmental condition" shall refer to conditions in the general proximity of an individual person. Environmental conditions may include indoor and/or outdoor conditions. Environmental conditions may include dangerous conditions. In addition environmental conditions may include primary conditions and secondary conditions, both of which are discussed in greater detail below.

The devices may collect data regarding location, speed, and direction. In addition, in some embodiments, the systems may be configured to monitor personal data regarding the wearer of the wearable devices, for example by collecting data from the wearable's heartrate monitor and/or pedometer, in order to assess the physical activity of the wearer. In some cases, the system may assess whether the wearer is running away from something, or scurrying about to prepare for an evacuation.

Additionally, or alternatively, in some embodiments, the system may be configured to collect atmospheric data, such as atmospheric temperature and/or atmospheric pressure, from the wearable device. Monitoring such parameters may enable the system to detect dangerous weather conditions, such as storms, etc.

The system may be configured to send instructions to avoid danger related to the detected conditions back to the wearable devices. The system may be configured to send instructions back to the same device from which received data was the basis for determining a particular condition. Additionally, or alternatively, the system may be configured to send instructions back to a different device than the device from which the received data was the basis for determining the condition. For example, if a forest fire is detected based on information received from a first device, instructions may be sent to a second device located further away from the fire than the first device, but still in the path of the fire.

In some embodiments, the system may be configured to collect data from multiple wearable devices in order to more accurately detect environmental conditions. Data from multiple devices may be used to determine patterns and/or to triangulate the location of an environmental condition. In such cases, the system may be configured to send instructions to any of the devices from which data is collected. Further, the system may be configured to send instructions to devices other than those from which data is used to detect an environmental condition.

Figure 1:
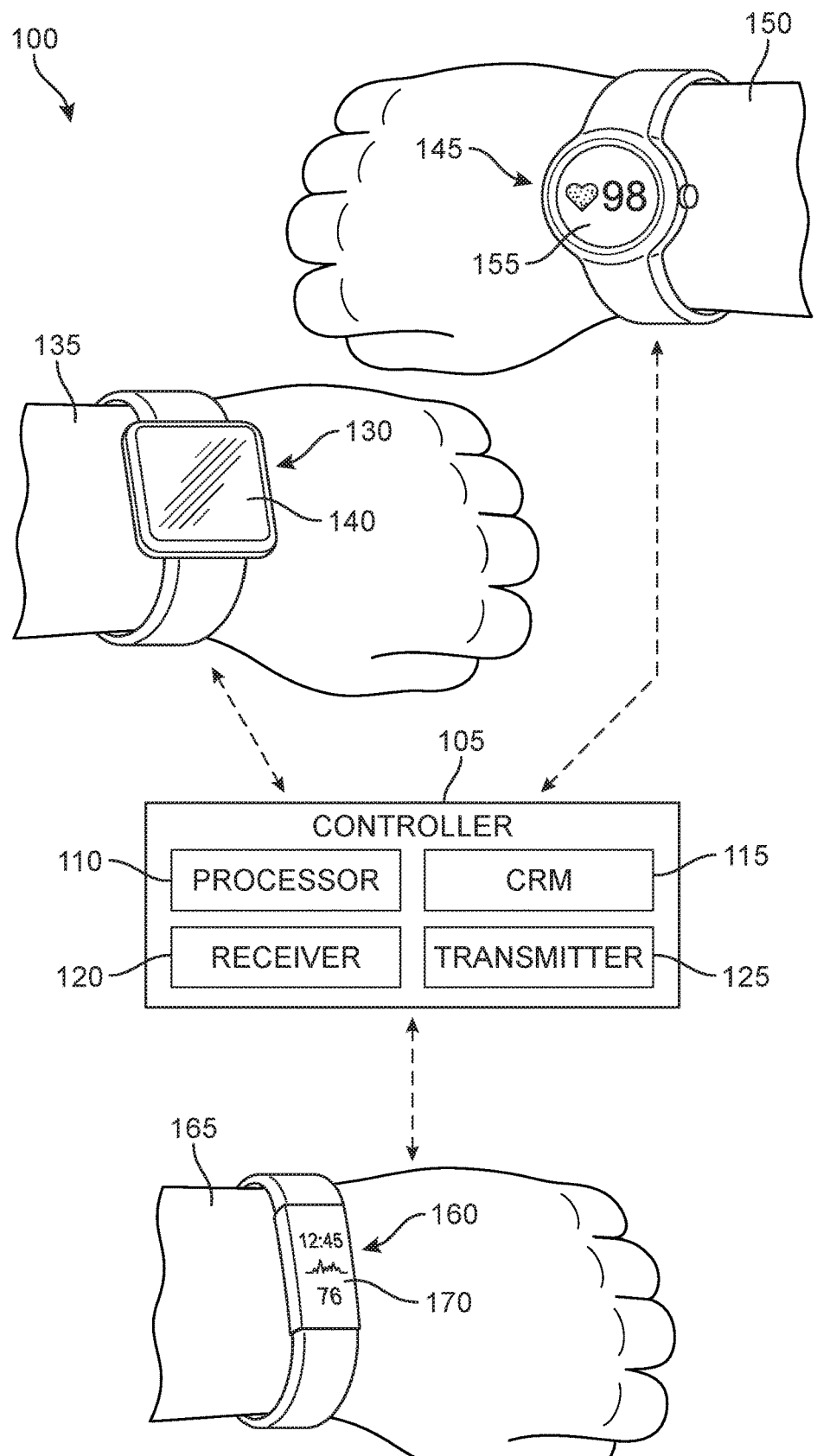
FIG. 1 is a schematic illustration of a conditions monitoring system.

FIG. 1 is a schematic illustration of a conditions monitoring system. In particular, FIG. 1 shows a conditions monitoring system 100. As shown in FIG. 1, system 100 may include a system controller 105. Controller 105 may include various computing and communications hardware, such as servers, integrated circuits, displays, etc. Further, controller 105 may include a device processor 110 and a non-transitory computer readable medium 115 including instructions executable by device processor 110 to perform the processes discussed herein. The components of controller 105 may be implemented in association with a mobile conditions monitoring center, such as vehicle, or in association with a control center or conditions monitoring center located in a temporary building (e.g., a portable trailer), or a permanent building (i.e., a brick and mortar establishment).

The non-transitory computer readable medium may include any suitable computer readable medium, such as a memory, e.g., RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, a read-only memory (ROM), a random access memory (RAM), a static random access memory (SRAM), a portable compact disc read-only memory (CD-ROM), an erasable programmable read-only memory (EPROM or Flash memory), a digital versatile disk (DVD), a memory stick, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

Controller 105 may include networking hardware configured to interface with other nodes of a network, such as a LAN, WLAN, or other networks. In Further, controller 105 may be configured to receive data from a plurality of sources and communicate information to one or more external destinations. Accordingly, controller 105 may include a receiver 120 and a transmitter 125. (It will be appreciated that, in some embodiments, the receiver and transmitter may be combined in a transceiver.)

Any suitable communication platforms and/or protocols may be utilized for communication between controller 105 and other components of the system. Since the various sources of information may each have their own platform and/or protocol, system 100 may be configured to interface with each platform and/or protocol to receive the data.

The computer readable medium may include instructions executable by the device processor to perform steps including receiving data from one or more devices. In some embodiments, computer readable medium may include instructions for receiving data from one or more wearable devices. For example, as shown in FIG. 1, system 100 may include a first wearable device 130, which may be worn by a first wearer 135. As further shown in FIG. 1, first wearable device 130 may include a first display 140 configured to display data, which may include instructions delivered to first wearable device from controller 105.

As shown in FIG. 1, system 100 may include a second wearable device 145, which may be worn by a second wearer 150. Second wearable device 145 may include a second display screen 155 configured to display data, which may include instructions delivered to first wearable device from controller 105. In addition, as also shown in FIG. 1, system 100 may include a third wearable device 160, which may be worn by a third wearer 165. Third wearable device 160 may include a third display screen 170 configured to display data, which may include instructions delivered to first wearable device from controller 105.

While FIG. 1 illustrates three wearable devices, system 100 may include any number of wearable devices. In addition, system 100 may include any of various types of wearable devices. As shown in FIG. 1, first wearable device 130 is illustrated as a smartwatch, second wearable device 145 is illustrated as a fitness watch, and third wearable device 160 is illustrated as a fitness band. In some embodiments, all devices of system 100 may be of the same type. In other embodiments, system 100 may include different types of devices as part of the same system, as shown in FIG. 1.

It will also be noted that each of the wearable devices in the present application are illustrated as being configured to be worn on the wrist of the wearer. However, in some embodiments, system 100 may include wearable devices worn on other parts of the body. For example, other types of wearable devices may be worn around the neck, arm, or waist; attached to clothing; or worn in any other manner.

Additionally, or alternatively, system 100 may include other types of devices besides wearable devices. For example, controller 105 may be configured to receive data from various Internet of Things (IoT) devices. Exemplary such devices may include various types of environmental sensors, such as temperature sensors, pressure sensors, moisture/humidity sensors, etc.

Each of the devices from which data is received by controller 105 may include a device processor and non-transitory computer readable medium containing instructions executable by the processor. Such devices may also include a receiver, transmitter, transceiver, or other communication equipment. Skilled artisans will readily recognize suitable features and specifications for such devices for use with the disclosed system.

Figure 2:
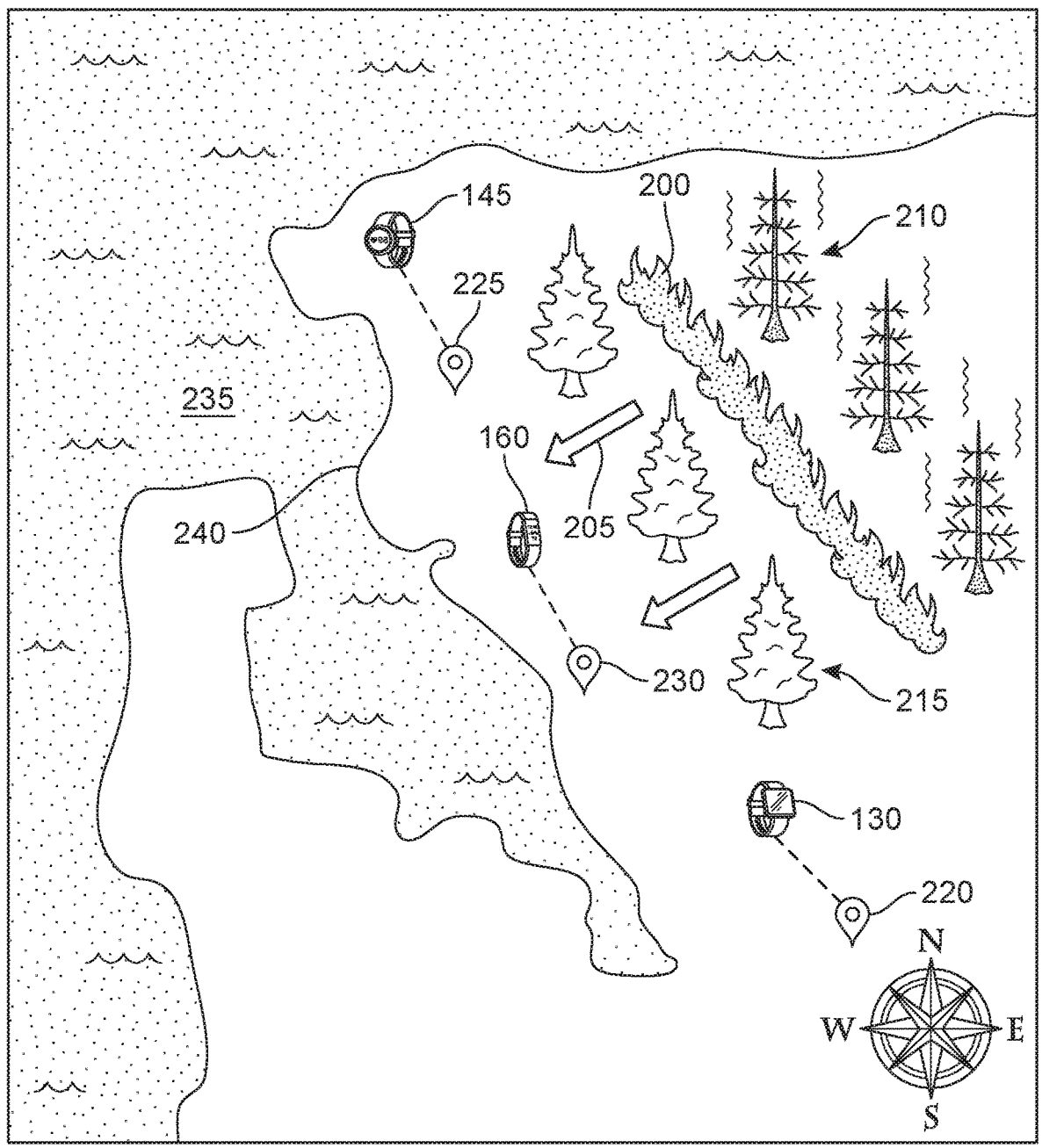
FIG. 2 is a schematic illustration of a map showing the locations of several wearers of data collecting wearable devices with respect to a proceeding forest fire.

FIG. 2 is a schematic illustration of a map showing the locations of several wearers of data collecting wearable devices with respect to a propagating forest fire. FIG. 2 shows, schematically, an example of how the disclosed system considers the location of a user with respect to a detected dangerous condition, such as a forest fire. As shown in FIG. 2, a map 200 illustrates a forest fire 200 proceeding in a direction indicated by an arrow 205. FIG. 2 further illustrates the progression of fire 200 with charred trees 210 where fire 200 has been, and unburned trees 215 ahead of fire 200.

A first pin location 220 indicates the position of first wearable device 130. As shown in FIG. 2, first pin location 220 of first wearable device 130 is outside the path of forest fire 200. A second pin location 225 indicates the position of second wearable device 145, and a third pin location 230 indicates the position of third wearable device 160. As shown in FIG. 2, second pin location 225 and third pin location 230 are located in the path of fire 200.

The disclosed system may be configured to detect the presence of fire 200 and, in some cases, the direction of propagation of fire 200. In order to determine the presence of fire 200, the system may detect not only the locations of the wearable devices, but also the speed and direction of each device. Accordingly, the system can detect whether the wearers are running, or otherwise moving, in a common direction. If multiple wearers are moving in a common direction, it may be determined that they are moving away from something, such as a dangerous condition.

Other data may also be interpreted to detect conditions. For example, in some embodiments, personal data about the wearer may be collected by the wearable devices and considered when determining the existence of dangerous conditions. For example, in some embodiments, the wearable devices may have sensors, such as heartrate monitors and pedometers. If an increase in heartrate and/or pedometer readings is detected, it may be a sign that wearers are fleeing some kind of dangerous condition, or preparing to do so. When considered in conjunction with the aforementioned location, speed, and direction data, a more accurate determination may be made that a dangerous condition is present, especially when data is considered from multiple wearable devices. With multiple devices, not only may the precise location of a dangerous condition be triangulated, but also the accuracy of the determination may be higher.

Once the presence and progression of a dangerous condition is determined by the system, messages may be delivered to the wearable devices with instructions related to the condition, such as directions for evading, or otherwise avoiding, the dangerous condition. In some cases, the wearer may be proximate to the dangerous condition, but not in its path. For example, as shown in FIG. 2, first wearable 130 is located at first pin location 220, which is not in the path of fire 200. Accordingly, the system may send a message to first wearable device 130 to display instructions informing the wearer that there is a fire nearby, but that they are in a safe location and do not need to evacuate.

As shown in FIG. 2, second wearable device 145 and third wearable device 160 are located in the path of fire 200. Therefore, the wearers of these two devices must evacuate. However, in this case, the wearers cannot simply evacuate directly away from fire 200 because there is a body of water 235 opposite fire 200. Notably, the distance that the wearers may evacuate to the west is limited by a coastline 240. Accordingly, the system may consider other geographic data when determining the best course of action for the wearers to avoid the danger. Thus, for second wearable device 145 and third wearable device 160, the system may send messages instructing the wearers to evacuate to the south southwest, which enables them to avoid the oncoming fire 200 despite the restriction of coastline 240 to the west southwest.

It will be noted that the dangerous condition detected may be any type of dangerous condition including, for example, dangerous weather, such as storms; natural disasters, such as earthquakes; and/or public emergencies, such as house fires or criminal activity.

Figure 3:
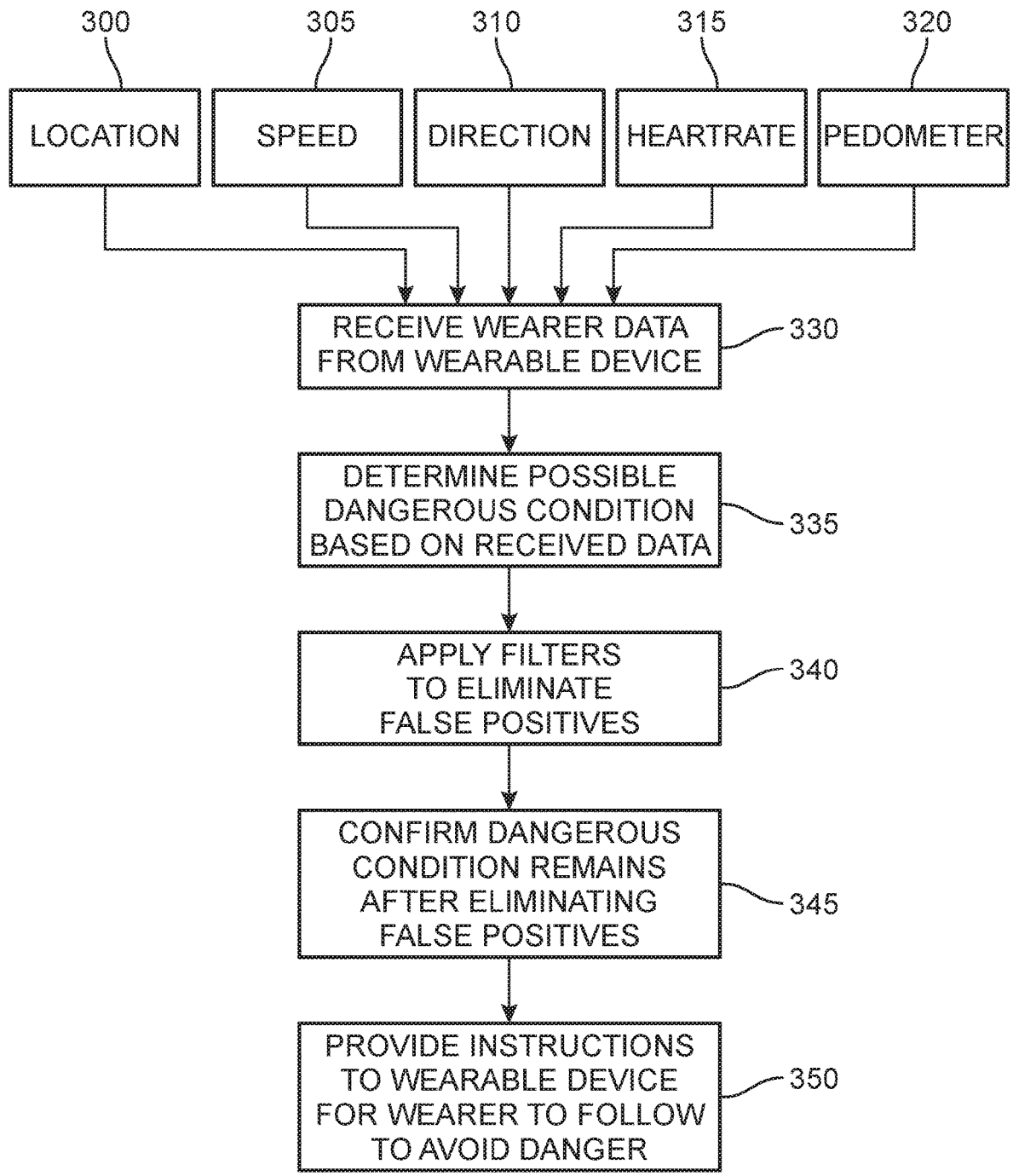
FIG. 3 is a flowchart showing a process of determining dangerous conditions based on data received from wearable devices.

FIG. 3 is a flowchart showing a process of determining dangerous conditions based on data received from wearable devices. As shown in FIG. 3, the system may receive several types of data from a wearable device. For example, in some embodiments, personal data may be received from the wearable device, such as data regarding the wearer's location 300, speed 305, and direction of movement 310. In addition, in some cases, physical data about the wearer may be received from the wearable device, such as the wearer's heartrate 315 and/or pedometer data 320. Data from these sources may be received from a wearable device at step 330. In addition, at step 335, upon receiving data from the wearable device, the system may determine one or more possible dangerous conditions based on the received data.

In order to eliminate false positives, the system may apply one or more filters at step 340. For example, the system may implement certain thresholds below which the system will not confirm a particular condition. For example, the system may have a minimum number of wearers that must be moving away from a common geographic location before a dangerous condition will be determined to exist at that location based on the apparent fleeing behavior of the wearers. Other filters may be used to avoid false positives accordingly. Once the filters have been applied, at step 345, the system may confirm the existence of a dangerous condition after eliminating any false positives with the filters. Finally, at step 350, the system may provide instructions to the wearable device for the wearer to follow to avoid danger related to the dangerous condition. For example, in some cases, the instructions may include directions evading the dangerous condition.

Figure 4:
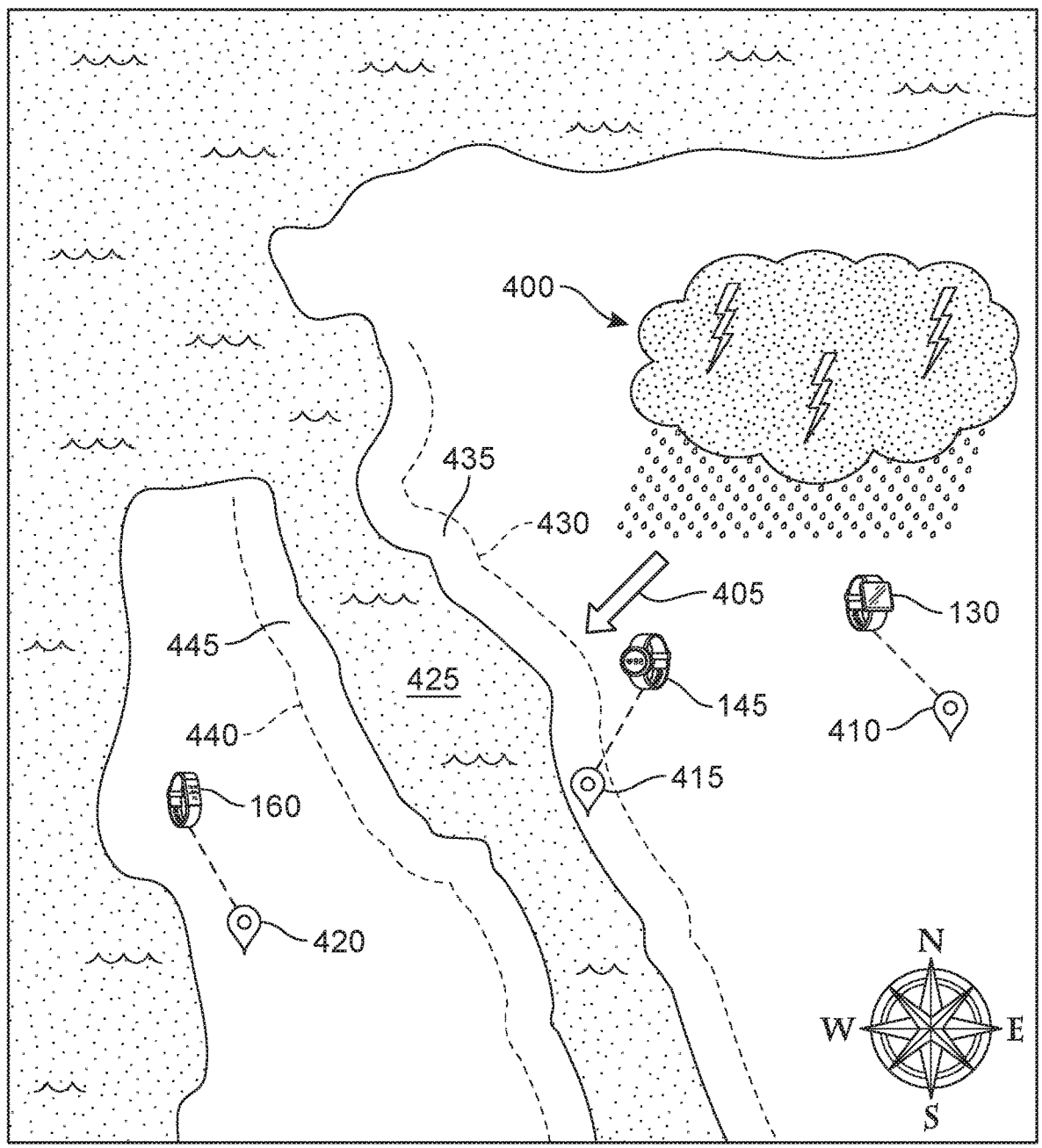
FIG. 4 is a schematic illustration of a map showing the locations of several wearers of data collecting wearable devices with respect to a thunderstorm and a predicted flood area.

FIG. 4 is a schematic illustration of a map showing the locations of several wearers of data collecting wearable devices with respect to a thunderstorm and a predicted flood area. FIG. 4 shows a thunderstorm 400 proceeds in a direction of arrow 405. FIG. 4 also shows first wearable device 130 at a first pin location 410, second wearable device 145 at a second pin location 415, and third wearable device 160 at a third pin location 420.

The computer readable medium of the system controller may include instructions for receiving positional data from the wearable devices. As with the embodiment discussed above, positional data may include, for example, location, speed, and direction of movement of the wearable devices. In addition, the computer readable medium may include instructions for receiving atmospheric data regarding the atmospheric in proximity to the wearer. In some embodiments, the atmospheric data may include, for example, atmospheric temperature and/or atmospheric pressure.

The system may be configured to make a determination of a possible dangerous condition based on the data received from one or more of the wearable devices. For example, as the speed and direction of monitored wearable devices reduces, it may indicate that there is a storm that causes wearers to seek shelter. Further, when such data is combined with a reduction in temperature and pressure, a stronger conclusion that a storm is either brewing or ongoing may be reached. Based on the location data of from the wearable devices, the location of the storm may be triangulated. Further, based on the changes in the data, the direction of movement of the storm may be determined.

In addition, the system may be configured to provide instructions to the wearable devices for the wearer to follow to avoid danger related to the dangerous condition. For devices outside the path of the storm, like first wearable device 130, a message may be sent alerting the wearer to the storm, but indicating that they are outside the path of the storm, and thus do not need to seek shelter. For devices, such as third wearable device 160 that fall within the path of the storm, a message may be sent to alert the wearer to the storm and provide instructions to seek shelter. The message may also provide directions to the nearest shelter available, in order to evade the danger associated with the storm.

As with the embodiment discussed above, it will be noted that the dangerous condition detected may be any type of dangerous condition including, for example, dangerous weather, such as storms; natural disasters, such as earthquakes; and/or public emergencies, such as house fires, criminal activity, rioting, chemical agents, etc.

In addition, as with the embodiment discussed above, one or more filters may be applied to the collected data in order to eliminate false positive determinations of dangerous conditions. For example, in the case of the thunderstorm, the rate at which the atmospheric pressure drops must be higher than a predetermined threshold in order for a storm to be determined. This eliminates false positives that may occur by simply monitoring barometric pressure, which may change significantly as part of a regular course of weather patterns. A sudden pressure drop over a period of minutes or hours, however, is more indicative of a storm than an equivalent pressure drop that occurs slowly over a period of days. Filters may be applied to ensure these factors are considered when determining the presence of dangerous conditions.

In some embodiments, the system may be configured to predict secondary conditions based on detected primary conditions, and provide instructions to wearers related to the secondary conditions. For example, if an oncoming storm is detected, the system will determine whether flooding is likely, and advise individuals in the area accordingly.

In some cases, the primary condition may not, itself, be necessarily dangerous, but may cause a dangerous secondary condition. For example, a simple rainstorm may not necessarily pose any danger to individuals in the area, but the rainstorm may cause flooding that does pose danger to certain individuals.

FIG. 4 shows a river 425 proceeding through the landmass. Alongside the river are a first boundary 430 illustrating a first floodplain 435 and a second boundary 440 illustrating a second floodplain 445. As shown in FIG. 4, second pin location 415 of second wearable device 145 is located within first floodplain 435. If first floodplain 435 routinely gets flooded during rainstorms, or if the rainstorm is predicted to drop a significant amount of rain, the system may send a message to second wearable device 145 advising to exit the floodplain. The instructions may be to evacuate toward the east northeast (i.e., directly away from the water. More specifically, the message may include navigation instructions, e.g., which roadways to take in order to exit first floodplain 435.

Figure 5:
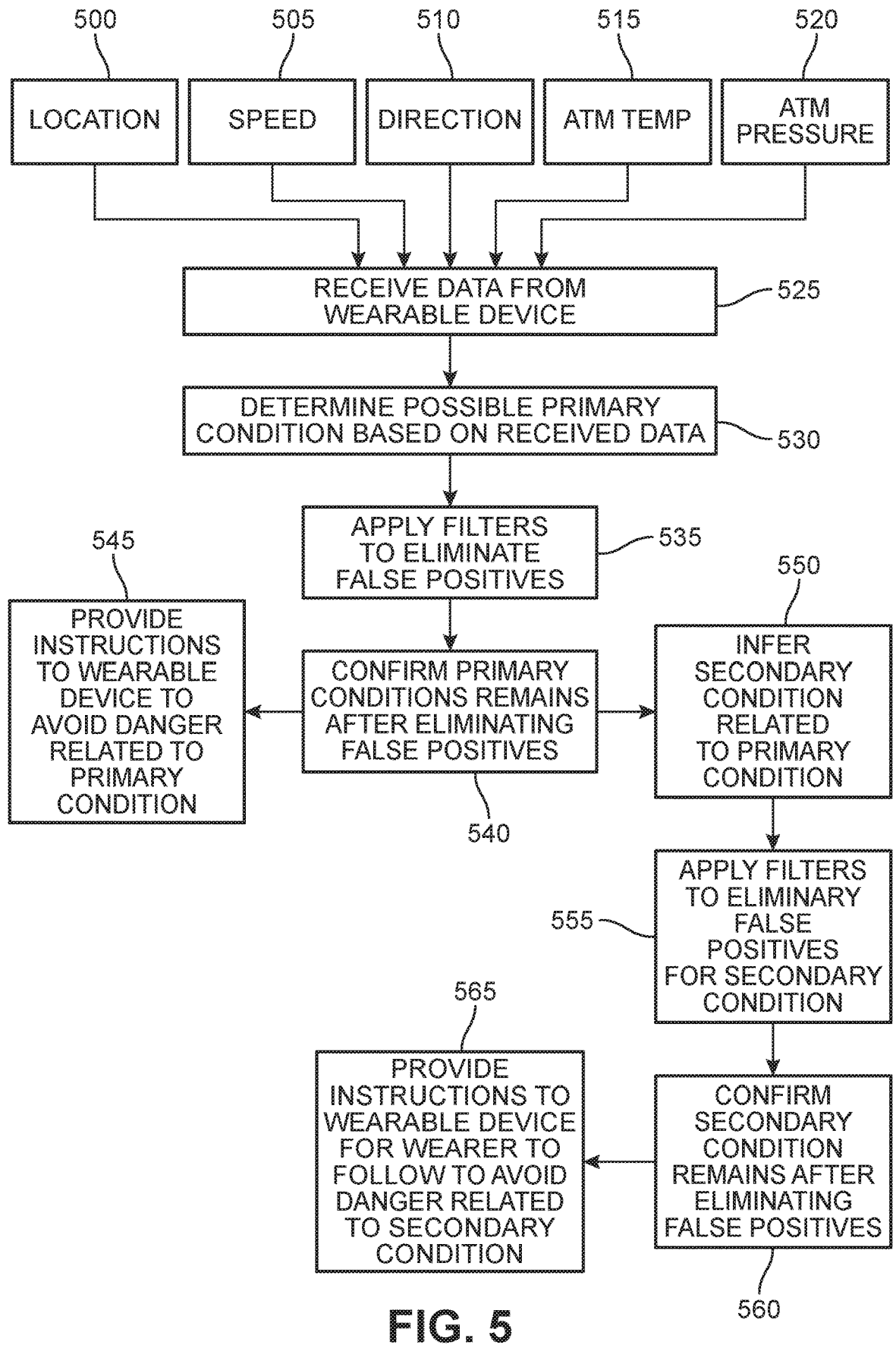
FIG. 5 is a flowchart illustrating a process of determining a primary condition and inferring a secondary condition based on the primary condition.

FIG. 5 is a flowchart illustrating a process of determining a primary condition and inferring a secondary condition based on the primary condition. As shown in FIG. 5, the system may receive several types of data from a wearable device. For example, in some embodiments, personal data may be received from the wearable device, such as data regarding the wearer's location 500, speed 505, and direction of movement 510. In addition, the system may be configured to collect atmospheric information from the wearable devices. For example, the system may be configured to receive atmospheric temperature 515 and/or atmospheric pressure 520.

At step 525, the system may receive the data from the wearable devices. Further, the computer readable medium of the system controller may include instructions for making a determination of a primary condition based on this data (and possibly other data) received from the wearable devices, as shown at step 530.

At step 535 one or more filters may be applied in order to eliminate false positive determinations of the primary condition. If, at step 540, the primary condition is confirmed to remain after eliminating potential false positives, the process proceeds to step 545, at which instructions are provided to one or more wearable devices to avoid danger related to the determined primary condition.

Additionally, or alternatively, the system may infer a secondary condition exists that is related to the primary condition. For example, as discussed above, if a thunderstorm is detected, then it may be inferred that a flood may occur soon. As shown in step 555, filters may also be applied to the determination of a secondary condition. If the secondary condition is confirmed, at step 560, to remain after elimination of potential false positives, the process proceeds to step 565, at which messages are sent to one or more wearable devices providing instructions for the wearer to follow in order to avoid danger related to the secondary condition.

It will be understood that the data collected from the wearable devices in any of the embodiments disclosed above may vary. Although location, speed, direction, heartrate, steps, atmospheric temperature, and atmospheric pressure are discussed above, it will be understood that other parameters may be collected from the wearable devices and considered by the controller in detecting conditions, including dangerous conditions, primary conditions, secondary conditions, etc. In addition, it will also be understood that other types of conditions may also be determined by the disclosed system besides those discussed herein. For example, in addition to, or instead of, forest fires, thunderstorms, and flooding, other conditions may be detected by the disclosed systems. In some cases, the data collected from the wearable devices may be different for detecting different conditions. In addition, in some embodiments, the system may be configured to detect more than one type of condition.

The embodiments discussed herein may make use of methods and systems in artificial intelligence to improve efficiency and effectiveness of the disclosed systems. As used herein, "artificial intelligence" may include any known methods in machine learning and related fields. As examples, artificial intelligence may include systems and methods used in deep learning and machine vision.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

We claim:

1. A conditions monitoring system, comprising:
 a system controller including:
  a device processor; and
  a non-transitory computer readable medium including instructions executable by the device processor to perform the following steps:
   receiving positional data from a wearable device of a wearer;
   receiving physical data regarding the wearer from the wearable device, wherein the physical data includes at least one of heartrate data and pedometer data;
   making a determination of a possible dangerous environmental condition based on the data received from the wearable device, including the positional data and the physical data; and
   providing instructions to the wearable device for the wearer to follow to avoid danger related to the dangerous environmental condition.

2. The system of claim 1, wherein the dangerous environmental condition includes at least one of dangerous weather, natural disaster, and public emergency.

3. The system of claim 1, wherein the positional data includes at least one of location, speed, and direction.

4. The system of claim 1, wherein the non-transitory computer readable medium further includes instructions for applying one or more filters to eliminate false positive determinations of possible dangerous environmental conditions.

5. The system of claim 1, wherein the instructions provided to the wearable device include directions for evading the dangerous environmental condition.

6. The system of claim 1, wherein the instructions are provided to a different wearable device than the wearable device from which the data is received.

7. The system of claim 1, wherein the non-transitory computer readable medium further includes instructions for receiving data from multiple wearable devices from multiple wearers and determining a dangerous environmental condition based on data received from the multiple wearable devices.

8. A conditions monitoring system, comprising:
 a system controller including:
  a device processor; and
  a non-transitory computer readable medium including instructions executable by the device processor to perform the following steps:
   receiving positional data from a wearable device of a wearer;
   receiving, from the wearable device, atmospheric data regarding the atmospheric conditions in proximity to the wearer;
   making a determination of a possible dangerous environmental condition based on the data received from the wearable device, including the positional data and the atmospheric data; and
   providing instructions to the wearable device for the wearer to follow to avoid danger related to the dangerous environmental condition.

9. The system of claim 8, wherein the dangerous environmental condition includes at least one of dangerous weather, natural disaster, and public emergency.

10. The system of claim 8, wherein the atmospheric data includes at least one of location, speed, and direction.

11. The system of claim 8, wherein the atmospheric data includes at least one of atmospheric temperature and atmospheric pressure.

12. The system of claim 8, wherein the non-transitory computer readable medium further includes instructions for applying one or more filters to eliminate false positive determinations of possible dangerous environmental conditions.

13. The system of claim 8, wherein the instructions provided to the wearable device include directions for evading the dangerous environmental condition.

14. The system of claim 8, wherein the instructions are provided to a different wearable device than the wearable device from which the data is received.

15. The system of claim 8, wherein the non-transitory computer readable medium further includes instructions for receiving data from multiple wearable devices from multiple wearers and determining a dangerous environmental condition based on data received from the multiple wearable devices.

16. A conditions monitoring system, comprising:
a system controller including:
   a device processor; and
   a non-transitory computer readable medium including instructions executable by the device processor to perform the following steps:
      receiving positional data from a wearable device of a wearer;
      receiving, from the wearable device, atmospheric data regarding the atmospheric conditions in proximity to the wearer;
      making a determination of a primary condition based on the data received from the wearable device, including the positional data and the atmospheric data;
      inferring, from the primary condition, a secondary condition related to the primary condition; and
      providing instructions to the wearable device for the wearer to follow to avoid a dangerous environment related to the secondary condition.

17. The system of claim 16, wherein the non-transitory computer readable medium further includes instructions for applying one or more filters to eliminate false positive determinations of the primary condition or the secondary condition.

18. The method of claim 16, wherein the primary condition is a storm and the secondary condition is a predicted flood.

19. The system of claim 16, wherein the instructions are provided to a different wearable device than the wearable device from which the data is received.

* * * * *